United States Patent [19]
Yamamoto

[11] Patent Number: 5,910,584
[45] Date of Patent: Jun. 8, 1999

[54] METHOD FOR ISOLATING PLASMID DNA

[75] Inventor: Akira Yamamoto, Tokyo, Japan

[73] Assignee: Asahi Kogaku Kogyo Kabushiki Kaisha, Tokyo, Japan

[21] Appl. No.: 08/922,356

[22] Filed: Sep. 3, 1997

[30] Foreign Application Priority Data

Sep. 5, 1996 [JP] Japan ................................ 8-235399

[51] Int. Cl.$^6$ ........................................ C07H 1/06
[52] U.S. Cl. ............................... 536/25.4; 536/25.41
[58] Field of Search ........................ 536/25.4, 25.41, 536/25.42

[56] References Cited

U.S. PATENT DOCUMENTS

| | | |
|---|---|---|
| Re. 35,267 | 6/1996 | Tsuru et al. . |
| 4,781,904 | 11/1988 | Tagaya et al. . |
| 4,830,969 | 5/1989 | Holmes . |
| 4,952,323 | 8/1990 | Nakabayashi et al. . |
| 4,956,298 | 9/1990 | Diekmann . |
| 4,981,952 | 1/1991 | Yan . |
| 5,039,408 | 8/1991 | Ichitsuka et al. . |
| 5,082,566 | 1/1992 | Tagaya et al. . |
| 5,085,781 | 2/1992 | Tsuru et al. . |
| 5,098,842 | 3/1992 | Nakajima et al. . |
| 5,208,160 | 5/1993 | Kikyotani et al. . |
| 5,484,720 | 1/1996 | Wurm et al. . |
| 5,540,995 | 7/1996 | Kitano et al. . |
| 5,651,884 | 7/1997 | Ichitsuka et al. . |

OTHER PUBLICATIONS

J. Chromatography, V. 238, pp. 307–316 (1982).
J. Biochemistry, V. 91, pp. 303–310 (1978).
J. Chromatography, V. 499, pp. 153–165 (1990).
Anal. Biochem., vol. 82, No. 2, pp. 633–637 (1978).

*Primary Examiner*—James O. Wilson
*Attorney, Agent, or Firm*—Greenblum & Bernstein, P.L.C.

[57] ABSTRACT

Method for isolating plasmid DNA, which comprises the steps of: suspending hydroxyapatite particles in a tris-EDTA buffer solution having a pH of about 7 to about 10, about 10 to about 50 mM of an EDTA alkali metal salt, and about 1 to about 100 mM of tris (hydroxymethyl) aminomethane; adding a solution containing RNA and plasmid DNA, obtained upon bacteriolysis, to the hydroxyapatite particles-containing suspension, thereby adsorbing the RNA onto the hydroxyapatite particles in the suspension; and recovering the plasmid DNA by an ethanol precipitation process and others. The isolation method enables effective separation of the purified plasmid DNA from a solution containing RNA and plasmid DNA in a simplified process, without the use for any special separation device.

7 Claims, No Drawings

METHOD FOR ISOLATING PLASMID DNA

BACKGROUND OF THE INVENTION

1. Field of the Invention

The present invention relates to a method for isolating a plasmid deoxyribonucleic acid (DNA) from nucleic acids which is one of the most basic operations in the field of genetic engineering.

2. Description of the Related Art

Hitherto, mass production of a target DNA by integrating and culturing the target DNA into a plasmid vector of coli bacteria (*Escherichia coli*) has been widely carried out in the field of genetic engineering.

At present, in the mass production of a target DNA the plasmid vector has been recovered from the coli bacteria by conducting bacteriolysis, followed by the removal of the genomic DNA, proteins, etc., to obtain a mixture of ribonucleic acid (RNA) and plasmid DNA. Some well-known methods for the recovery of the plasmid vector include an alkali-SDS (sodium dodecyl sulfate) method, etc. Furthermore, in order to obtain a purified plasmid DNA from the mixture of RNA and plasmid DNA, a column separation method using an ion-exchange resin, a density-gradient centrifugation method using cesium chloride and the like, have generally been used as the separation method.

However, the above-mentioned separation methods have several drawbacks. For example, since the target plasmid DNA is obtained after having been diluted with a voluminous amount of an eluting solution, the column separation method using an ion-exchange resin requires a troublesome concentration of the eluted plasmid DNA. Furthermore, since centrifugation must be carried out in a large scale centrifugal apparatus at a high revolution for a long period of time, the density-gradient centrifugation method requires the greatest of care which makes centrifugation troublesome and uneconomical.

SUMMARY OF THE INVENTION

An object of the present invention is to provide an isolation method which enables an effective separation of purified plasmid DNA from a solution containing RNA and plasmid DNA in a simplified process without the need for any special separation device.

As a result of their diligent studies and research, the inventors of the present invention have found that if a buffer solution having a specific pH range, with an alkali metal salt of ethylenediaminetetraacetic acid (EDTA) having a specific concentration, and with tris(hydroxymethyl)aminomethane having a specific concentration is prepared and the resulting buffer solution is used in the separation of the purified plasmid DNA from a solution containing RNA and plasmid DNA, the RNA can be adsorbed on particles of a calcium phosphate compound, however the plasmid DNA is not adsorbed on the same particles. Based upon this finding, the inventors have completed the present invention which will be described hereinafter in detail.

According to the present invention, there is provided a method for isolating a plasmid DNA, which includes:

suspending particles of a calcium phosphate compound having a Ca/P ratio of about 1.0 to about 2.0 in a buffer solution having a pH of about 7 to about 10, about 10 to about 50 mM alkali metal salt of EDTA, and about 1 to about 100 mM tris(hydroxymethyl)aminomethane to obtain a calcium phosphate particles-containing suspension;

adding a solution containing an RNA and plasmid DNA, obtained upon bacteriolysis, to the calcium phosphate particles-containing suspension, thereby adsorbing the RNA onto the calcium phosphate particles in the suspension; and recovering the plasmid DNA from a supernatant of the suspension.

According to the present invention, there is also provided a method for isolating plasmid DNA in accordance with liquid chromatography, which includes the steps:

filling a chromatographic column with particles of a calcium phosphate compound having a Ca/P ratio of about 1.0 to about 2.0;

equilibrating the column of the calcium phosphate particles with a buffer solution having a pH of about 7 to about 10, about 10 to about 50 mM alkali metal salt of EDTA, and about 1 to about 100 mM Tris (hydroxymethyl)aminomethane;

passing a solution containing RNA and plasmid DNA, obtained upon bacteriolysis, and then a buffer solution having a pH of about 7 to about 10, about 10 to about 50 mM alkali metal salt of EDTA, and about 1 to about 100 mM tris(hydroxymethyl)aminomethane; and recovering the plasmid DNA from an eluate of the column.

The present disclosure relates to subject matter contained in Japanese Patent Application No. 08-235399 (filed on Sep. 5, 1996) which is expressly incorporated herein by reference in its entirety.

PREFERRED EMBODIMENTS OF THE PRESENT INVENTION

In the practice of the present invention, the particles of a calcium phosphate compound having a Ca/P ratio of about 1.0 to about 2.0 are suspended in the above-described buffer solution or are filled in a chromatographic column. The calcium phosphate compound used herein is not restricted to the one specified, insofar as it has a Ca/P ratio of about 1.0 to about 2.0, and typical examples thereof include one or more members selected from the group consisting of hydroxyapatite, fluoroapatite, tribasic calcium phosphate, tetrabasic calcium phosphate and others, i.e., $Ca_{10}(PO_4)_6(OH)_2$, $Ca_{10}(PO_4)_6F_2$, $Ca_{10}(PO_4)_6Cl_2$, $Ca_3(PO_4)_2$, $Ca_2P_2O_7$, $Ca_4O(PO_4)_2$, $CaHPO_4$ and others. Among the above-listed calcium phosphate compounds, it is preferred to use a calcium phosphate compound having a Ca/P ratio of about 1.5 to about 1.8 in view of obtaining a good stability and adsorption property, and more preferably a calcium phosphate compound which contains a hydroxyapatite having a Ca/P ratio of about 1.67 as a principal component thereof. When fluoroapatite is used, it is preferred to adjust a fluorine content in the fluoroapatite to not more than 5% by weight, based on a total amount of the calcium phosphate compounds.

A fluorine content above 5% by weight should be avoided, because it can cause an undesirable dissolution of fluorine from the fluoroapatite. The calcium phosphate compounds can be produced in accordance with any one of the well-known methods.

The particles of a calcium phosphate compound (hereinafter, also referred to as "calcium phosphate particles") used in the present invention preferably have an average particle diameter of about 1 micron($\mu$m) to about 1 millimeter(mm) and a specific surface area, determined in accordance with the BET (Brunauer-Emmett-Teller) method, of about 1 to about 300 m$^2$/g, and more preferably, about 5 to about 300 m²/g. Regarding the calcium phosphate particles, an average particle diameter of less than 1 μm can result in difficulty in the handling of the particles, and a specific surface area of less than 1 m²/g may not ensure a satisfactory adsorptivity due to low specific surface area. On the other hand, an average particle diameter of more than 1 mm and a specific surface area of more than 300 m²/g can cause a reduction of the filling density and formation of non-uniform aggregate products, respectively, and thus the properties of the particles are deteriorated.

The above-described calcium phosphate compounds can be produced by synthesizing the compounds from different types of calcium compounds and phosphoric acid compounds as the starting materials, followed by granulating and drying the obtained calcium phosphate compounds and then classifying the dried particles. Sometimes, it becomes necessary to prepare the particles as porous granules in order to obtain particles satisfying the above-described requirements. Such granular calcium phosphate particles can be prepared using any conventional production method.

In the isolation method according to the present invention, in order to selectively adsorb the RNA of the nucleic acid components onto the above-described calcium phosphate particles, while not adsorbing the plasmid DNA of the same components, a buffer solution having about 10 to about 50 mM alkali metal salt of EDTA and about 1 to about 100 mM tris(hydroxymethyl)aminomethane is prepared, and to the resulting solution, calcium phosphate particles having a Ca/P ratio of about 1.0 to about 2.0 are added and suspended. Then, to the resulting calcium phosphate particles-containing suspension, a solution containing an RNA and a plasmid DNA obtained upon bacteriolysis, is added. The bacteriolysis can be carried out by using any well-known method such as an alkali-SDS method or the like. Upon the bacteriolysis, genomic DNA of the coli bacteria as well as proteins and lipids, i.e., constitutional components of the bacterium body, are removed, thus producing a solution containing principally the remaining plasmid DNA and RNA.

Tris(hydroxymethyl)aminomethane used in the present invention has a concentration of about 1 to about 100 mM. A concentration of less than 1 mM is generally not enough to compensate for a pH of the solution due to the absence of the buffering action, while a concentration above 100 mM can cause adsorption of the plasmid DNA onto the calcium phosphate particles. Further, in the present invention, about 10 to about 50 mM, preferably about 20 to about 40 mM of alkali metal salt of EDTA is present in the buffer solution. If the concentration of the alkali metal salt of EDTA is less than 10 mM, adsorption of the RNA onto the calcium phosphate particles may not be achieved, and if the concentration is above 50 mM, adsorption of both the plasmid DNA and the RNA onto the calcium phosphate particles, is possible.

In addition, it is preferred that a pH of the buffer solution which may be prepared by adding an alkali metal salt of ethylenediaminetetraacetic acid (hereinafter, also referred to as EDTA) to a buffer solution of tris(hydroxymethyl) aminomethane ((hereinafter, also referred as a tris-buffer solution), the prepared solution also being referred to as a tris-EDTA buffer solution), is adjusted to have a range of about 7 to about 10. A pH of less than 7 can significantly reduce adsorption of the RNA onto the calcium phosphate particles, and a pH of more than 10 can cause an undesirable adsorption of the plasmid DNA onto other particles. Namely, using the buffer solution having the described pH range according to the present invention, it becomes possible to selectively adsorb only the RNA onto the calcium phosphate particles, while retaining the plasmid DNA, with a high accuracy, in the solution. The preparation of the tris-EDTA buffer solution having the described pH range can be advantageously attained by starting with a tris(hydroxymethyl) aminomethane buffer solution having a pH of about 5 to about 9. For example, the pH value of the solution can then be controlled to be within the described range by using an alkali such as about 0.1M sodium hydroxide or the like, and/or using an acid such as hydrochloric acid or the like. It is more preferrable that sodium hydroxide is contained in the tris-EDTA buffer solution, because sodium hydroxide can dissolve EDTA.

The EDTA is present in the tris-EDTA buffer solution mainly for the purpose of causing an inactivation of the nuclease. In addition to this function, the EDTA, when used in the present invention, can surprisingly simultaneously exhibit another remarkable function. Namely, since calcium ions are liberated from the calcium phosphate compound, the RNA can be adsorbed on the particles of the calcium phosphate compound, and at the same time, the plasmid DNA can be retained in the tris-EDTA buffer solution without being adsorbed.

According to the present invention, since the RNA in the nucleic acid components can be selectively adsorbed on the particles of the calcium phosphate compound, and the plasmid DNA can be retained in the tris-EDTA buffer solution, the plasmid DNA can be easily recovered using an alcoholic precipitation method using an alcohol such as ethanol, or by other recovery methods.

Alternatively, the plasmid DNA can be easily isolated from other nucleic acid components by using the above-described particles of the calcium phosphate compound as a filling material in a column for the chromatography, followed by conducting a liquid chromatographic process using the filled column. In the liquid chromatographic process, the plasmid DNA is not adsorbed on the filling material of the column, and therefore it is contained in the eluate which is then discharged from the column.

In carrying out the chromatographic process, the column is filled with the particles of the calcium phosphate compound and, after equilibration, a test solution containing both the RNA and the plasmid DNA is passed through the column to conduct a separation operation. In this chromatographic process, it is preferred that the tris-EDTA buffer solution used in the equilibration step and the subsequent separation step has the same concentration and pH value.

The present invention will be further described with reference to working examples thereof. Note, however, that the present invention should not be restricted to these examples.

EXAMPLES 1 TO 11 AND COMPARATIVE EXAMPLES 1 TO 5 pBulescriptSK(+) (trademark of Stratagene) having an ampicillin-resistant gene was transformed to a JM 109 competent cell which was then cultured in a LB-agar medium containing 50 μg/mL of ampicillin at 37° C. for a whole day and night to obtain a single colony species. The colony species were then cultured by shaking in a LB culture solution containing 50 μg/mL of ampicillin at 37° C. for a whole day and night to obtain a bacterium body. After centrifugal separation, the bacterium body was treated with an alkali-SDS method to prepare a mixed solution of plasmid DNA and RNA having a nucleic acid concentration of 200 μg/mL (hereinafter, referred to as a "test solution").

A tris-EDTA buffer solution was prepared by adding sodium ethylenediaminetetraacetate (NaEDTA) to a buffer solution of tris(hydroxymethyl)aminomethane-hydrochloride (tris-buffer solution) to obtain concentrations of tris and EDTA shown in Table 1, then adjusting the pH of the obtained tris-EDTA buffer solution with 0.1M sodium hydroxide to a level shown in Table 1.

After the preparation of the tris-EDTA buffer solution having the described pH level, 20 mg of hydroxyapatite particles having an average particle diameter of about 20 microns and a specific surface area, determined in accordance with the BET method, of about 50 m²/g, were suspended in 70 μL of the tris-EDTA buffer solution. Then, 15 μL of the test solution was added to the obtained suspension and the suspension was shaken for five minutes at room temperature. Thereafter, a supernatant was recovered from the suspension, and then subjected to a gel electrophoretic process using 0.8% agarose gel. An analysis of the nucleic acid components was made with dying using ethidium bromide to obtain the results shown in the following Table 2.

TABLE 1

| Example solution No. | tris conc. | EDTA conc. | tris-EDTA buffer pH |
|---|---|---|---|
| Compar. Ex. 1 | 10 mM | 1 mM | 7 |
| Ex. 1 | 10 mM | 10 mM | 7 |
| Ex. 2 | 10 mM | 20 mM | 7 |
| Ex. 3 | 10 mM | 50 mM | 7 |
| Ex. 4 | 100 mM | 20 mM | 9 |
| Ex. 5 | 50 mM | 20 mM | 9 |
| Ex. 6 | 30 mM | 20 mM | 9 |
| Ex. 7 | 10 mM | 20 mM | 9 |
| Ex. 8 | 100 mM | 40 mM | 10 |
| Ex. 9 | 50 mM | 40 mM | 10 |
| Ex. 10 | 30 mM | 40 mM | 10 |
| Ex. 11 | 10 mM | 40 mM | 10 |
| Compar. Ex. 2 | 100 mM | 20 mM | 6 |
| Compar. Ex. 3 | 50 mM | 20 mM | 6 |
| Compar. Ex. 4 | 30 mM | 20 mM | 6 |
| Compar. Ex. 5 | 10 mM | 20 mM | 6 |

TABLE 2

| Example No. | adsorption on hydroxyapatite | |
|---|---|---|
| | plasmid DNA | RNA |
| Compar. Ex. 1 | not adsorbed | not adsorbed |
| Ex. 1 | not adsorbed | adsorbed |
| Ex. 2 | not adsorbed | adsorbed |
| Ex. 3 | slightly adsorbed | adsorbed |
| Ex. 4 | not adsorbed | adsorbed |
| Ex. 5 | not adsorbed | adsorbed |
| Ex. 6 | not adsorbed | adsorbed |
| Ex. 7 | not adsorbed | adsorbed |
| Ex. 8 | not adsorbed | adsorbed |
| Ex. 9 | not adsorbed | adsorbed |
| Ex. 10 | not adsorbed | adsorbed |
| Ex. 11 | not adsorbed | adsorbed |
| Compar. Ex. 2 | not adsorbed | not adsorbed |
| Compar. Ex. 3 | not adsorbed | not adsorbed |
| Compar. Ex. 4 | not adsorbed | not adsorbed |
| Compar. Ex. 5 | not adsorbed | not adsorbed |

As can be appreciated from the results shown in Table 2, a purified plasmid DNA having a high purity could be obtained using a tris-EDTA buffer solution having a pH of 7 to 10, obtained by adding an alkali metal salt of ethylenediaminetetraacetic acid (EDTA) to a buffer solution of tris(hydroxymethyl)aminomethane (tris-buffer solution) to obtain 10 to 50 mM EDTA and 1 to 100 mM tris. In particular, good results could be obtained when the EDTA was used at a concentration of 20 to 40 mM.

EXAMPLE 12

A chromatographic column was filled with hydroxyapatite particles having an average particle diameter of about 20 microns and a specific surface area, determined in accordance with the BET method, of about 50 m²/g, and then the column was washed with a tris-EDTA buffer solution having a concentration and pH level similar to that used in Example 2. Further, a test solution, identical to the mixed solution of plasmid DNA and RNA used in Example 1 was prepared upon bacteriolysis in accordance with the manner described in Example 1.

The test solution and the tris-EDTA buffer solution in a thrice amount of the capacity of the column were used as an eluting solution, and the eluting solution was passed through the column. The eluting solution was then recovered from the column and subjected to a gel electrophoretic process using 0.8% agarose gel, and then the nucleic acid components were analyzed with dying using ethidium bromide. The presence of the plasmid DNA could be confirmed from the results of the analysis.

According to the isolation method of the present invention, as will be appreciated from the above descriptions, a purified plasmid DNA can be easily obtained from a solution containing an RNA and a plasmid DNA, obtained upon bacteriolysis, in a simplified operation and without the need for any special apparatus. Further, contrary to the prior art methods such as a column separation method using an ion-exchange resin, the isolation method of the present invention can be carried out in a reduced number of operation steps, since an eluting operation is not necessary, and the plasmid DNA can be easily concentrated and purified in accordance with an alcoholic precipitation method or the like.

What is claimed is:

1. A method for isolating a plasmid deoxyribonucleic acid, comprising:

suspending particles of a calcium phosphate compound having a Ca/P ratio of about 1.0 to about 2.0 in a buffer solution having a pH of about 7 to about 10, about 10 to about 50 mM of an alkali metal salt of ethylenediaminetetraacetic acid, and about 1 to about 100 mM of tris(hydroxymethyl)aminomethane, to obtain a calcium phosphate particles-containing suspension;

adding a solution containing ribonucleic acid and plasmid deoxyribonucleic acid, obtained upon bacteriolysis, to said calcium phosphate particles-containing suspension, thereby adsorbing said ribonucleic acid onto the calcium phosphate particles in said calcium phosphate particles-containing suspension; and recovering said plasmid deoxyribonucleic acid from a supernatant of said calcium phosphate particles-containing suspension.

2. The method for isolating a plasmid deoxyribonucleic acid according to claim 1, in which a pH of said buffer solution is adjusted by adding an acid and/or an alkali.

3. The method for isolating a plasmid deoxyribonucleic acid according to claim 1, in which said particles of a calcium phosphate compound have an average particle diameter of about 1 micron to about 1 millimeter and a specific surface area of about 1 to about 300 m²/g.

4. A method for isolating a plasmid deoxyribonucleic acid, comprising:

filling a chromatographic column with particles of a calcium phosphate compound having a Ca/P ratio of about 1.0 to about 2.0;

equilibrating said column of the calcium phosphate particles with a buffer solution having a pH of about 7 to about 10, about 10 to about 50 mM of an alkali metal salt of ethylenediaminetetraacetic acid, and then about 1 to about 100 mM of tris(hydroxymethyl)aminomethane;

passing a solution containing ribonucleic acid and plasmid deoxyribonucleic acid, obtained upon bacteriolysis, and a buffer solution having a pH of about 7 to about 10, about 10 to about 50 mM of an alkali metal salt of ethylenediaminetetraacetic acid, and about 1 to about 100 mM of tris(hydroxymethyl) aminomethane, through said column; and recovering said plasmid deoxyribonucleic acid from an eluate of said column.

5. The method for isolating a plasmid deoxyribonucleic acid according to claim 4, in which said buffer solution of alkali metal salt of ethylenediaminetetraacetic acid and tris(hydroxymethyl)aminomethane used in each of said equilibration steps and subsequent separation steps has the same concentration and pH value.

6. The method for isolating a plasmid deoxyribonucleic acid according to claim 4, in which a pH of said buffer solution is adjusted by adding an acid and/or an alkali.

7. The method for isolating a plasmid deoxyribonucleic acid according to claim 4, in which said particles of a calcium phosphate compound have an average particle diameter of about 1 micron to about 1 millimeter and a specific surface area of about 1 to about 300 $m^2/g$.

* * * * *